United States Patent
Leser

(10) Patent No.: US 7,181,861 B1
(45) Date of Patent: Feb. 27, 2007

(54) PORTABLE LINEAR MEASURING DEVICE

(76) Inventor: Christian F. Leser, P.O. Box 3, Burlingham, NY (US) 12722

( * ) Notice: Subject to any disclaimer, the term of this patent is extended or adjusted under 35 U.S.C. 154(b) by 29 days.

(21) Appl. No.: 11/062,260

(22) Filed: Feb. 18, 2005

(51) Int. Cl.
*G01B 3/22* (2006.01)

(52) U.S. Cl. .............................. 33/832; 33/512; 33/494

(58) Field of Classification Search .......... 33/832–833, 33/511–512, 515, 492, 483–485, 783, 806, 33/809–812, 759, 494
See application file for complete search history.

(56) References Cited

U.S. PATENT DOCUMENTS

| | | | | |
|---|---|---|---|---|
| 1,741,174 A | * | 12/1929 | Weber | 33/8 |
| 2,215,884 A | | 9/1940 | Runge | 33/169 |
| 2,410,696 A | * | 11/1946 | Wheeler | 33/484 |
| 3,313,030 A | | 4/1967 | Heys | 33/169 |
| 4,134,212 A | | 1/1979 | Allen | 33/169 R |
| 5,402,585 A | | 4/1995 | Lund | 33/832 |
| 5,996,240 A | | 12/1999 | Casper | 33/759 |
| 6,073,359 A | | 6/2000 | Lee | 33/759 |
| 6,226,881 B1 | | 5/2001 | Landauer | 33/515 |
| 6,237,239 B1 | | 5/2001 | Miyazaki | 33/512 |

* cited by examiner

Primary Examiner—Yaritza Guadalupe-McCall
(74) Attorney, Agent, or Firm—Sandra M. Kotin

(57) ABSTRACT

A device to measure the height of a person consists of an elongated base that extends from above the head of the person being measured to the flat surface on which the person stands and a sliding member. The base has two longitudinal channels, one containing a T-track and the other a measuring scale. There is a blank surface on which to record the height and other additional data. Decorative indicia may also be placed on the blank area. The vertically movable sliding member has a forward extending bar that rests against the top of the head of the person being measured. A follower extends from the side of the sliding member across the channel containing the scale. The top edge of the follower is at the same level as the bottom surface of the bar. The height can be read along the top edge of the follower. The sliding member has a threaded bolt extending through it with a tab on the back end which is movable within the T-track and prevents the sliding member from being pulled out of the T-track. A knob on the front end of the bolt is rotated to retain the sliding member in a specific location. The sliding member is removable from the elongated base member for storage. The base has a hole near the top for attachment to a vertical surface. The device can be used anywhere as long as it rests on a flat surface and can be supported in a vertical orientation.

13 Claims, 3 Drawing Sheets

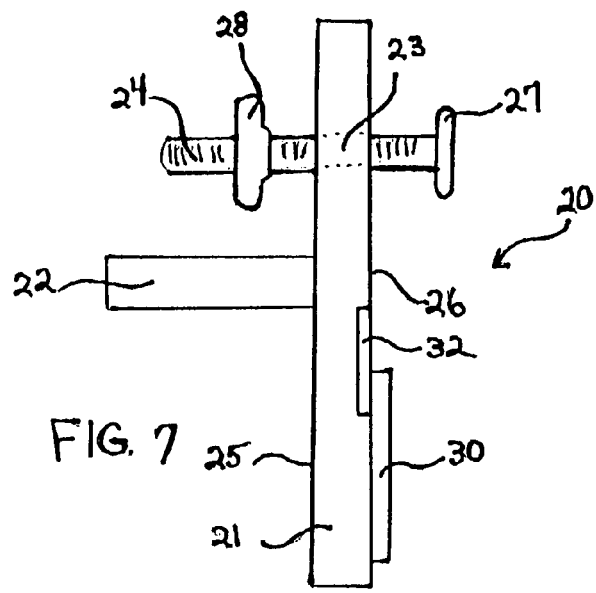
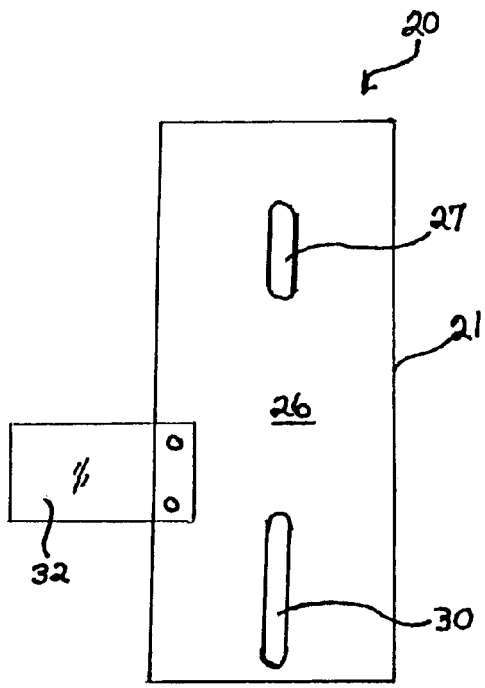
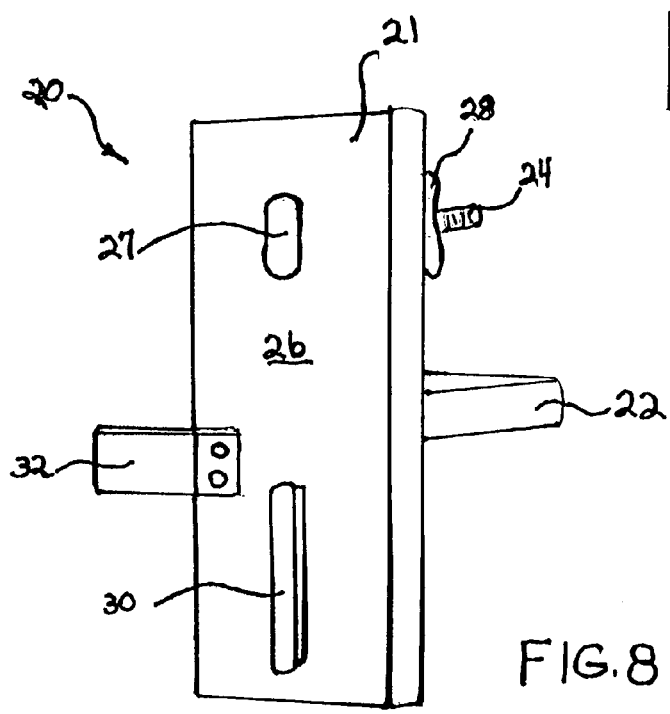

PORTABLE LINEAR MEASURING DEVICE

FIELD OF THE INVENTION

The instant invention relates to a portable device to accurately measure and record the height of a person.

BACKGROUND OF THE INVENTION

It is common for parents to measure the growth of their children. This has often been accomplished by having the child stand against a wall, holding a pencil against the child's head and making a mark on the wall. The distance from the mark to the floor is thereafter measured using a yardstick or tape measure. The mark can then be removed, or left in place for comparison to future such marks. There are boards designed to be fastened to the wall, reach to the floor and have graduations printed on them. The child stands against the board and the parent makes a mark on the board. If the board is wide enough the date and name of the child can also be written on it. Often these boards are decorated with cartoon characters or sports motifs. They have no moving parts. Other more complex devices have been developed to measure the height of both children and adults.

Runge, in U.S. Pat. No. 2,215,884 teaches a device to measure the height of a child that consists of a board with a graduated scale that reads zero at the bottom and increases numerically upward. There are deep notches on both sides of the board to accommodate a movable forward projecting plate. There is a beveled section in the center of the plate that intersects with the reading on the graduated scale. The board is hung on a wall at an appropriate height so that the head of the child is against the board. The plate is moved to rest on the child's head. A mark can be made next to the graduation to denote the height. This board records changes in growth only, and to determine the actual height the distance from the zero marking to the floor must be measured and added to the reading on the board. The plate can be folded down so it is flat against the board when not in use.

Allen, in U.S. Pat. No. 4,134,212, discloses a measuring device that must be wall mounted at a predetermined distance from the floor. A flat panel has lateral flanges that engage a vertically movable head member with a head plate that extends forward to rest on the head of the person being measured and folds flat when not in use. An axle is rotated to move the head member along the panel and a friction wheel prevents unwanted movement of the head member. A series of pins of different colors are attached to the head member and a name can be inscribed next to each pin. When a measurement is made a colored sticker representing a particular named person can be placed at the level of the head plate to record the height. A book can be maintained in the head member to record any additional information.

The device of Lund, described in U.S. Pat. No. 5,402,585, has a flat base to be mounted on a wall and includes a 35 inch rod. The 35 inch notation on the scale of the flat base is aligned with the top of the rod and the bottom of the rod touches floor. When the base is mounted, the height of the person being measured can be read from a scale on the base. A movable horizontal arm supported on the base with a biasing spring is moved to contact the top of the head of the person being measured. Measurements from 21 inches to 84 inches can be made.

Landauer describes a measuring device that has a base made up of two linear segments hinged together in the middle. There is a sliding forward extending member that can be moved over both segments and scale notations on the two segments. There is no place to record data. A 24 inch leg slides into the lower segment. The leg must be fully extended and must touch the floor when the base is attached to the wall so that the scale will provide an accurate measurement. (U.S. Pat. No. 6,226,881)

Lee (U.S. Pat. No. 6,073,359) discloses a measuring device that is attached to a wall or other vertical surface and does not reach the floor. A movable measuring marker with a forward extension is held in place by magnetic attraction. There is no place to record measurements on the base. The marker is hinged so that the forward extension can be folded against the base when not in use.

Another measuring device is composed of three parts, a base member that must be stuck to a wall about 30 inches above the floor by means of an adhesive, a slidable indicator and a flexible steel measuring tape. There are two tracks in the base member. The tape is unrolled and slid upward into one track and the indicator is placed in the other track. The indicator is moved so that it touches the head of the person being measured and the person steps away so the height can be read. There is no place to record the height on the tape. (Heys, U.S. Pat. No. 3,313,030) The device of Casper (U.S. Pat. No. 5,996,240) is personal to one child and has three parts, a top housing with a space for a picture of the child, a ribbon with the scale marked on it, and a foot plate. The child steps on the plate and the ribbon is unrolled until the top housing rests on the child's head. A shaft can be turned to make the ribbon taut and a mark can be made on the ribbon under the housing to indicate the height. Miyazaki describes a similar three part measuring device. This one utilizes a punch to make a hole in the tape to note the height and a space to mark the date or name of the child next to the punch hole after the child steps away. (U.S. Pat. No. 6,237,239) The latter two measuring devices require the person being measured to stand against a wall when the device is used, though the device is not attached to the wall.

All of the prior art patents require that the devices be attached to a wall or used against a wall. In the devices using a flexible tape, one end of the tape must be placed perfectly on the floor and there can be no slack if an accurate reading is to be obtained. The other devices are attached to a wall but do not extend to the floor. Various means are used to account for the distance from the device to the floor and measurements may not be exact. Many of the prior art devices require the assistance of another person to take the measurement, and most do not provide enough space to record data such as the date, name of subject and other desired information.

There is a need for a measuring device that gives an accurate measurement of the subject and one that the subject can use alone. There is a need for such a measuring device that also provides sufficient space to record any necessary data with each measurement. There is also a need for a measuring device that does not have to be attached to a wall in order to get an accurate measurement and can be stored and brought out only when needed.

BRIEF SUMMARY OF THE INVENTION

The present invention provides a measuring device that can accurately measure the height of an individual. The device also has space to mark and record the height as well as to note pertinent information such as, but not limited to the name of the person being measured, the date of the measurement and the significance of the particular date.

It is an object of the present invention to provide a measuring device that can give an accurate height measurement of the person being measured.

Another object of the present invention is to provide a device that a person can use with out the assistance of another person.

A further object of the present invention is to provide a measuring device that has sufficient space to record a measurement and other significant data on the device.

A still further object of the present invention is to enable the device to be used without the necessity of mounting the device on a wall or other vertical structure.

Another object of the present invention is to provide a measuring device that consists of two parts which can be separated from one another for storage.

It is also an object of the present invention to provide a device that has a movable member that can be securely maintained at the exact point of the measurement to facilitate the recording of the measurement and other data at the proper location.

The present invention is a device for measuring the height of a person that comprises an elongated rigid base member having a front surface, a first longitudinal edge and a second longitudinal edge. There is a first longitudinal channel disposed along the full length of the front surface of the elongated base member substantially adjacent to the first longitudinal edge, a T-track disposed within the first longitudinal channel, a second longitudinal channel disposed along the full length of the front surface of the elongated base member, and a measuring scale disposed within the second longitudinal channel. The entire length of the front surface of the elongated base member adjacent the second longitudinal edge is a blank area means for the application of marks, data and decorations. A sliding member capable of movement along the T-track comprises a flat base member having a front face and a rear face, a horizontal measuring bar having an upper surface and a lower surface, affixed to the front face of the flat base member, and extending forwardly therefrom. The flat base member has an aperture situated above the horizontal measuring bar and a bolt having a front end and a rear end is disposed within the aperture and extends forwardly and rearwardly of the flat base member. There is a tab affixed to the rear end of the bolt. The tab is dimensioned to be slidably retained within the T-track. A movable retaining means is disposed on the forward end of the bolt for retaining the sliding member at a specified vertical location along the elongated base member. When the base member is vertically oriented on a flat surface, the slide is moved vertically along the T-track until the lower surface of the measuring bar rests against the head of the person to be measured and the retaining means is moved so as to retain the sliding member at that specific location, the height of the person can be obtained by noting the level of the lower surface of the measuring bar and reading the measurement from the measuring scale.

A device for measuring the height of a person also comprises an elongated rigid base member having a front surface, a first longitudinal edge, and a second longitudinal edge. The base member extends from a point above the head of the person to be measured to a flat surface on which the device is positioned. There is a first longitudinal channel disposed along the full length of the front surface of the elongated base member substantially adjacent to the first longitudinal edge, a T-track disposed within the first longitudinal channel, a second longitudinal channel disposed along the full length of the front surface of the elongated base member, a measuring scale disposed within the second longitudinal channel, a blank area means along the entire length of the front surface of the elongated base member adjacent the second longitudinal edge for the application of marks, data and decorations. There is a sliding member capable of movement along the T-track that comprises a flat base member having a front face and a rear face, a horizontal measuring bar having an upper surface and a lower surface, being affixed to the front face of the flat base member, and extending forwardly therefrom, and an aperture in the flat base member situated above the horizontal measuring bar. A threaded bolt having a front end and a rear end is disposed within the aperture and extends forwardly and rearwardly of the flat base member. A tab is affixed to the rear end of the bolt and the tab is dimensioned to be slidably retained within the T-track. A knob having a threaded bore therethrough is disposed on the forward end of the bolt for retaining the sliding member at a specified vertical location along the elongated base member. When the base member is vertically oriented on the flat surface, the slide is moved vertically along the T-track until the lower surface of the measuring bar rests against the head of the person to be measured and the knob is rotated until the sliding member is retained at that specific location, the height of the person can be obtained by noting the level of the lower surface of the measuring bar and reading the measurement from the measuring scale.

Other features and advantages of the invention will be seen from the following description and drawings.

BRIEF DESCRIPTION OF THE DRAWINGS

FIG. 7 is a right side plan view of the sliding member;

FIG. 8 is rear perspective view of the sliding member; and

FIG. 9 is rear plan view of the sliding member.

DETAILED DESCRIPTION OF THE INVENTION

Figure 1:
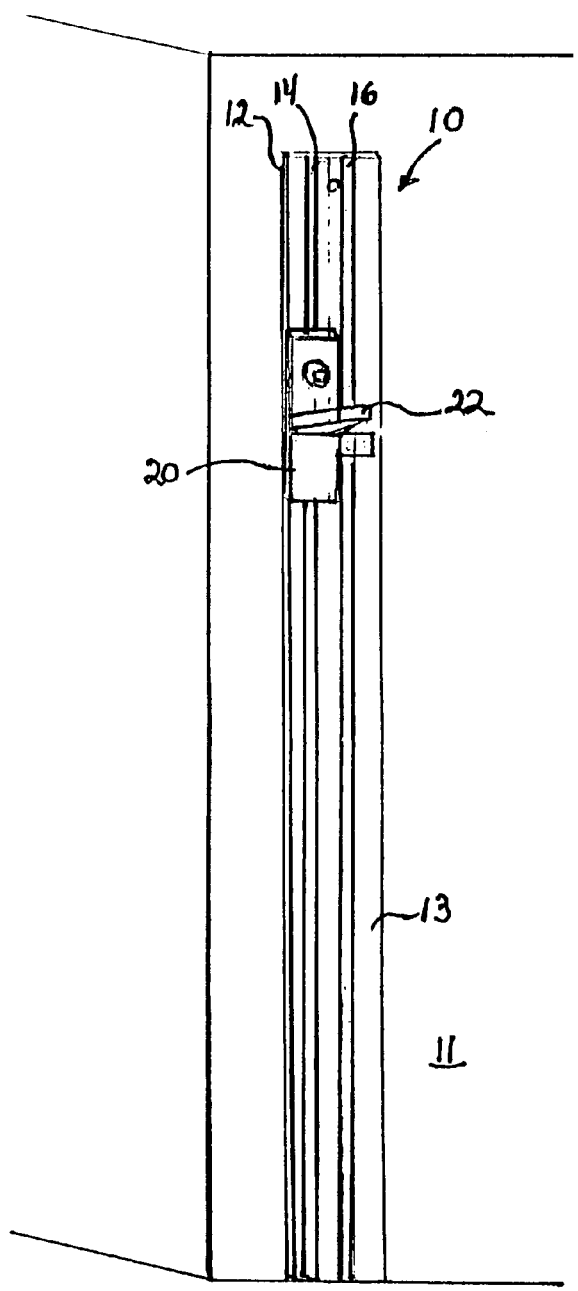
FIG. 1 is a perspective view of the measuring device of the present invention.

The measuring device 10 of the present invention may be seen in FIG. 1 situated against a wall 11. There may be an elongated base 12 with two longitudinal channels in the front surface 13. The first channel 14 may be closer to the left side of the base and may be deep and wide enough to accept a T-track 15. The second channel 16 may overlap the mid-line of the base and may contain a measurement scale 17. Both the first channel 14 and the second channel 16 may extend the full length of the elongated base 12.

Figure 3:
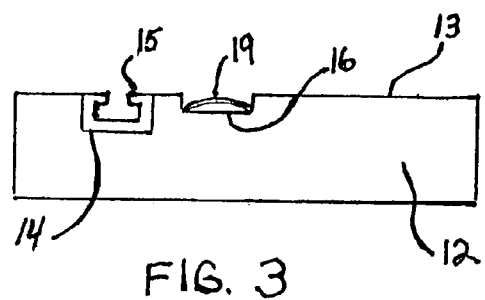
FIG. 3 is a section through line 3—3 of FIG. 1.
Figure 4:
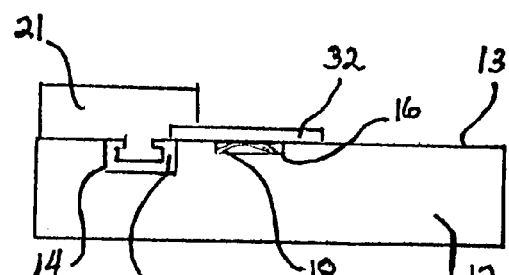
FIG. 4 is a section through line 4—4 of FIG. 1.
Figure 2:
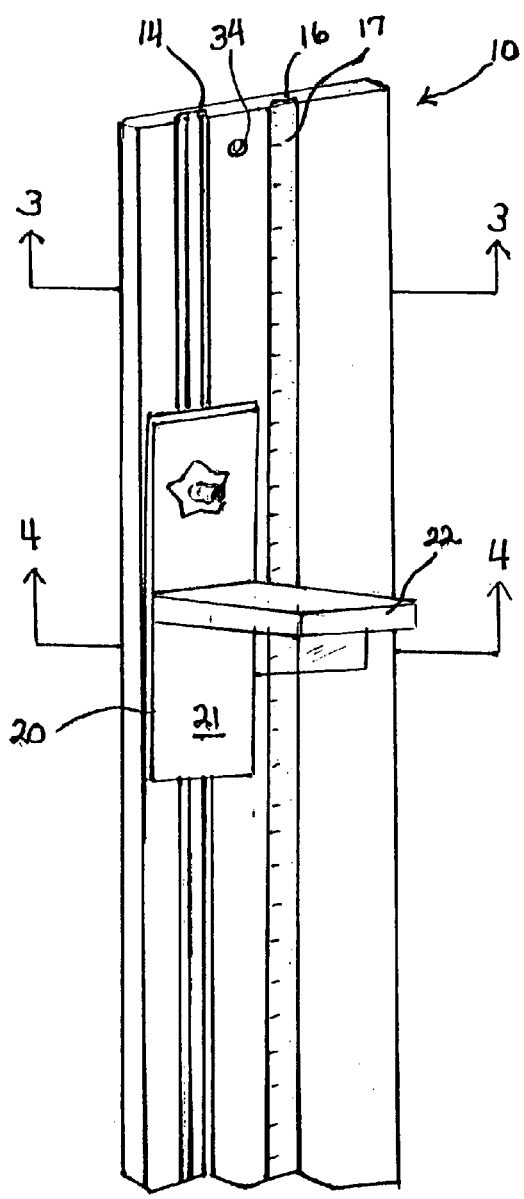
FIG. 2 is a close up perspective view of a portion of the device of FIG. 1.

The measurement scale 17 may be any linear scale, and may include one or both of the conventional English scale marked in feet and inches and the metric scale marked in meters and centimeters. The linear scale may be applied or painted directly on the base within the second channel 16 or a readily available measuring tape may be affixed to the elongated base 12 within the second channel 16. Typically, a metal tape measure 18 exhibiting both the English and metric scales may be utilized. The metal tape measure 18 may be affixed to the base at the bottom and extended upward and fastened at the top with the entire tape lying within the second channel 16. The depth of the second channel 16 may be just sufficient to contain the metal tape measure 18 and deep enough so that the metal tape measure 18 does not extend upward beyond the edges of the second channel 16. Most metal tape measures are somewhat concave in cross section and may not lie flat on a surface. The second channel 16 may be dimensioned to accommodate this concavity 19 which may be seen in FIGS. 3 and 4. Even if the measurement scale 17 is applied or painted directly onto the base, it may be desirable that the scale be recessed, i.e., applied within the second channel 16, so that the scale may not become scratched or rubbed off with continued use.

The remaining right side of the front surface of the elongated base 12 may be left blank and may provide space to record any pertinent data such as, but not limited to, the height and name of person being measured, the date the measurement was made, any significance of that date (such as a birthday), and even the attachment of a photograph of the person being measured. This area may also be decorated with a variety of design elements.

There may also be a T-shaped member or slide 20 affixed within the T-track 15 and capable of vertical movement along the full length of the T-track 15. The slide 20 may have a flat base 21 and a forward projecting member or measuring bar 22 substantially centered on the flat base 21. Centered above the measuring bar 22 may be a bore 23 through the flat base 21. A threaded bolt 24 may be situated within the bore 23 and extend forward beyond the front surface 25 of the flat base 21 and rearward beyond the rear surface 26 of the flat base 21. An oval tab 27 may be attached to the rear end of the bolt 24. The tab 27 may be configured to be disposed within the T-track 15 when vertically aligned therein. The tab 27 may be freely moved vertically within the T-track 15 but may not be withdrawn from the T-track except by passing it to either end and slipping it out. There may be a knob 28 with a threaded bore 29 therethrough which may be threaded onto the front end of the bolt 24. The knob 28 may be rotated until the flat base 21 is flush with the front surface 13 of the elongated base 12 and the slide 20 is prevented from further vertical movement. Centered below the measuring bar 22 and affixed to the rear surface 26 of the flat base 21 may be an elongated guide 30. The guide 30 may be fitted into the T-track 15 from the front and may be vertically movable within the T-track 15 over its full length.

The entire slide 20 may be completely removable from the elongated base 12 of the device 10 for transport and/or storage by loosening the knob 28 and moving the slide to either end of the elongated base 12 and removing the tab 27 from the T-track 15. The slide 20 may be attached to the elongated base 12 by sliding the tab 27 into the T-track 15 from either the top or bottom end of the elongated base 12. The guide 30 may then be placed into the T-track 15 and the knob 28 tightened on the bolt 24 until the rear surface 26 of the flat base 21 of the slide 20 rests against the front surface 13 of the elongated base 12. Once the knob 28 is tightened, the slide 20 may remain in place until the knob 28 is loosened and the slide moved up or down to another location.

Figure 5:
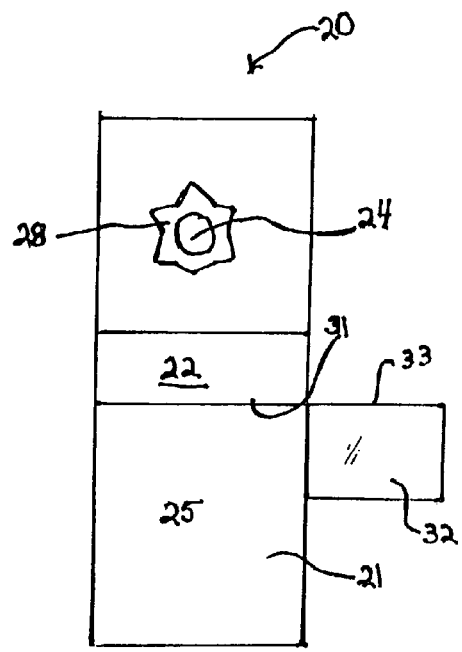
FIG. 5 is a front plan view of the sliding member.
Figure 6:
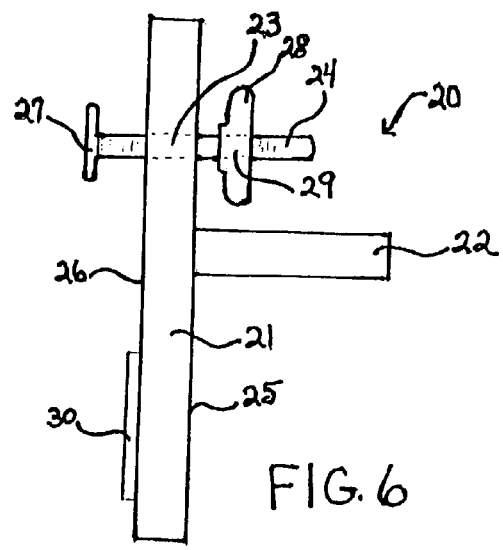
FIG. 6 is a left side plan view of the sliding member.

The measuring bar 22 may extend forward far enough to permit the bottom surface 31 of the measuring bar to rest comfortably on the head of the person being measured when that person stands against the vertically oriented elongated base 12. The distance from the bottom surface 31 of the measuring bar 22 to the floor may be the height of the person. To make it easier to note the measurement and record it on the right side of the front surface 13 of the elongated base 12, a follower 32 may be affixed to the rear surface 26 of the slide 20 and may extend from the right side of the slide 20 over the second channel 16. To insure that the presence of the follower 32 does not interfere with the smooth vertical movement of the slide 20, the follower 32 may be recessed into the rear surface 26 of the slide 20 so that it may be co-planar therewith. The upper edge 33 of the follower 32 may be exactly level with the bottom surface 31 of the measuring bar 22 as seen in FIG. 5. The follower 32 may be transparent so that the scale may be completely visible at all times. The recessing of the metal tape measure 18 within the second channel 16 may also facilitate the ease of movement of the follower 32 over the front surface 13 of the elongated base 12.

In use, the slide 20 may be installed into the T-track 15 of the elongated base 12 as described above, and the elongated base 12 maintained in a vertical orientation which may be facilitated by resting it against a flat vertical surface such as a wall 11. The person to be measured may stand against the elongated base 12 and the slide 20 moved along the T-track 15 until the bottom surface 31 of the measuring bar 22 just rests on the top of his or her head. The knob 28 may then be tightened on the bolt 24 until the slide 20 is held fast in that location. The height may be read from the scale 17 along the upper edge 33 of the follower 32. A mark or line may be drawn along the upper edge 33 of the follower 32 directly onto the front surface 13 of the elongated base 12. This line may denote the exact measurement of the height of the person. Any additional information may be written on the front surface 13 of the elongated base 12 near the line. As long as the slide 20 is not moved, the line may be drawn after the person steps away from the device 10. A person may take his or her own height measurement as long as the device 10 is maintained in the vertical orientation and rests on a flat surface. The assistance of another person may be needed to support the device 10 against a wall 11 and to hold it in place while the measurement is being made, or the device 10 may be fastened to a wall. There may be an opening 34 in the center of the elongated base 12 near the top edge. The elongated base 12 may be placed flat against a wall 11 resting on the floor and a nail or screw may be inserted into the opening 34 and fastened into the wall. If the head of the nail or screw is smaller than the opening 34, the device 10 may be removed and replaced onto the nail or screw as needed.

Since the device 10 does not have to be attached to a wall it may be stored in any convenient location and brought out only when needed. The device 10 does not have to be supported against a vertical surface. With the assistance of another person to support it in a vertical orientation the device 10 may be used anywhere as long as it rests on a flat surface large enough for the device 10 and for the person being measured to stand against the elongated base 12. The device 10 may be used in many places such as gyms, schools or spas, as well as in the home.

Measuring devices such as the device 10 of the present invention may be desired by parents to record the growth of their children, and this device 10 with space to record information may be used for all of the children in a family, or it may be used in a class or other children's group or club. However, there are other family needs that may be met by this device 10. With more people becoming aware of osteoporosis, many may benefit from having such a device in the home. As noted above, a person may take and record his or her own height periodically and note any changes before a condition becomes serious.

Typically the elongated base 12 may be made from a length of wood that may be 5.5 in (13.97 cm) wide, 0.75 in (1.90 cm) thick and 78 in (198.12 cm) long. The side edges may be rounded and sanded for a pleasing appearance. The first channel 14 for the T-track 15 may be located 0.75 in (1.90 cm) from the left edge and may be 0.75 in (1.90 cm) wide and 0.375 in (0.95 cm) deep. The T-track may fit tightly into the first channel 14 and may be retained therein by countersinking 0.373 in (0.95 cm) #6 flat head screws along the length of the T-track. There may be 1 in (2.54 cm) between the first channel 14 and the second channel 16. The second channel 16 may be 0.75 in (1.90 cm) wide and 0.125 in (0.32 cm) deep and may accept a metal tape measure as previously noted. These measurements may leave an area 2.25 in (5.72 cm) wide over the full length of the elongated base 12 on which to record data and/or place decorative designs.

The flat base 21 of the slide 20 may be made from a piece of wood that may be 9.0 in (22.86 cm) long, 2.0 in (5,08 cm) wide, and 0.75 in (1.90 cm) thick. The measuring bar 22 may be 2.0 in (5.08 cm) wide, 0.75 in (1.90 cm) thick and may be 6 in (15.24 cm) long. The measuring bar 22 may be affixed to the base 21 at a point 5 in (12.70 cm) from the top edge. The attachment may be by any means known in the art. One method may be to make a recess in the front surface 25 of the flat base 21, two holes through the flat base 21, and two holes in one end of the measuring bar 22 so that two 0.25 in (0.64 cm) dowels may be inserted through the flat base 21 from the rear and into the holes in the end of the measuring bar 22 to anchor the measuring bar 22 in place. The measuring bar 22 may extend forward some 6 in (15.24 cm) less the depth of the recess in the front face of the flat base 21. The follower 32 may be 1.0 in (2.54 cm) high and 2.0 in (5.08 cm) wide and may be seated in a recess in the rear surface 26 of the flat base 21. The setting of the measuring bar 22 and the follower 32 must be exact since the top edge of the follower 32 must be even with the bottom surface of the measuring bar 22 to provide an accurate measurement. The follower may be made of any rigid material, but a transparent plastic such as lexan may work well.

The guide 30 may be at least 2.0 in (5.08 cm) long and just wide enough and thick enough to be slidably situated within the T-track 15. The guide 30 may be affixed to the center of the lower rear surface 26 of the flat base 21 by any suitable means known in the art. A 0.25 in (0.63 cm) hole centered in the flat base 21 about 2.5 in (6.35 cm) from the top edge may accept a threaded bolt 24 that may be at least 2.5 in (6.35 cm) long with an oval tab 27 affixed to one end. The oval tab 27 may be wide enough to be slidable within the T-track 15, but not wide enough to be removable from the front of the T-track 15, and at least 0.75 in (1.90 cm) long. The knob 28 may be any suitable threaded knob that fits the threaded bolt 24 and is easy to rotate by persons of all ages and abilities.

The wood surfaces may be painted or stained and a finishing coat of polyurethane or other such material may be applied to preserve the finish.

Though the measuring device 20 described herein may be carefully hand made of wood, it may just as easily be made of plastic, metal or any other rigid material. If an injection molded plastic is used the T-track may be built into the plastic negating the need to insert a separate T-track.

The length of the elongated base 12 has been described above as 78 in (198.12 cm) which may accommodate children and most adults. However, the elongated base 12 may be shorter to measure only young children, or longer to measure athletes and very tall individuals. The length may be determined by the prospective use. Other dimensions for the base and the slide may be chosen to accommodate specific needs. The measuring device 20 may also be used to measure primates and other animals.

While one embodiment of the present invention has been illustrated and described in detail, it is to be understood that this invention is not limited thereto and may be otherwise practiced within, the scope of the following claims.

I claim:

1. A device for measuring the height of a person comprising:
    an elongated rigid base member having a front surface, a first longitudinal edge
    and a second longitudinal edge;
        a first longitudinal channel disposed along the full length of the front surface of the elongated base member substantially adjacent to the first longitudinal edge;
        a T-track disposed within the first longitudinal channel;
        a second longitudinal channel disposed along the full length of the front surface of the elongated base member;
        a measuring scale disposed within the second longitudinal channel;
        a blank area means along the entire length of the front surface of the elongated base member adjacent the second longitudinal edge for the application of marks, data and decorations;
        a sliding member capable of movement along the T-track comprising:
            a flat base member having a front face and a rear face;
            a horizontal measuring bar having an upper surface and a lower surface, being affixed to the front face of the flat base member, and extending forwardly therefrom;
            an aperture in the flat base member situated above the horizontal measuring bar;
            a bolt having a front end and a rear end, disposed within said aperture, and extending forwardly and rearwardly of the flat base member;
            a tab affixed to the rear end of the bolt, said tab dimensioned to be slidably retained within the T-track;
            movable retaining means disposed on the front end of the bolt for retaining the sliding member at a specified vertical location along the elongated base member;
    whereby when the base member is vertically oriented on a flat surface, the slide is moved vertically along the T-track until the lower surface of the measuring bar rests against the head of the person to be measured and the retaining means is moved so as to retain the sliding member at that specific location, the height of the person can be obtained by noting the level of the lower surface of the measuring bar and reading the measurement from the measuring scale.

2. A device as in claim 1 wherein the sliding member further comprises guide means affixed to the rear face of the flat base member for insertion into the T-track and for guiding the sliding member along the T-track as the siding member is moved vertically.

3. A device as in claim 1 wherein the sliding member further comprises a follower attached to the flat base member at a point below the measuring bar and extending in the same plane as the rear surface of the flat base member and across the second longitudinal channel, said follower having an upper horizontal edge at the same level as the lower surface of the measuring bar, whereby the height of the person being measured can be read along the upper edge of the follower.

4. A device as in claim 1 wherein the bolt is threaded.

5. A device as in claim 4 wherein the retaining means comprises a knob having a threaded aperture therethrough to co-act with the threaded bolt.

6. A device as in claim 1 wherein the elongated base member extends from a point above the head of the person being measured to a flat surface on which the device is positioned.

7. A device as in claim 1 wherein the measuring scale is permanently applied to the inside of the second longitudinal channel.

8. A device for measuring the height of a person comprising:
- an elongated rigid base member having a front surface, a first longitudinal edge, and a second longitudinal edge, said base member extending from a point above the head of the person to be measured to a flat surface on which the device is positioned;
- a first longitudinal channel disposed along the full length of the front surface of the elongated base member substantially adjacent to the first longitudinal edge;
- a T-track disposed within the first longitudinal channel;
- a second longitudinal channel disposed along the full length of the front surface of the elongated base member;
- a measuring scale disposed within the second longitudinal channel;
- a blank area means along the entire length of the front surface of the elongated base member adjacent the second longitudinal edge for the application of marks, data and decorations;
- a sliding member capable of movement along the T-track comprising:
  - a flat base member having a front face and a rear face;
  - a horizontal measuring bar having an upper surface and a lower surface, being affixed to the front face of the flat base member, and extending forwardly therefrom;
  - an aperture in the flat base member situated above the horizontal measuring bar;
  - a threaded bolt having a front end and a rear end, disposed within said aperture, and extending forwardly and rewardly of the flat base member;
  - a tab affixed to the rear end of the bolt, said tab dimensioned to be slidably retained within the T-track;
  - a knob habing a threaded bore therethrough disposed on the forward end of the bolt for retaining the sliding member at a specified vertical location along the elongated base member;
- whereby when the base member is vertically oriented on the flat surface, the slide is moved vertically along the T-track until the lower surface of the measuring bar rests against the head of the person to be measured and the knob is rotated until the sliding member is retained at that specific location, the height of the person can be obtained by noting the level of the lower surface of the measuring bar and reading the measurement from the measuring scale.

9. A device as in claim 8 wherein the sliding member further comprises guide means affixed to the rear face of the flat base member for insertion into the T-track and for guiding the sliding member along the T-track as the sliding member is moved vertically.

10. A device as in claim 8 wherein the sliding member further comprises a follower attached to the flat base member at a point below the measuring bar and extending in the same plane as rear surface of the flat base member and across the second longitudinal channel, said follower having an upper horizontal edge at the same level as the lower surface of the measuring bar, whereby the height of the person being measured can be read along the upper edge of the follower.

11. A device as in claim 8 wherein the measuring scale is permanently applied to the inside of the second longitudinal channel.

12. A device as in claim 8 wherein the elongated base member further comprises an upper edge, a lower edge and an aperture adjacent the upper edge.

13. A device as in claim 8 wherein the horizontal measuring bar is substantially vertically centered on the front face of the flat base member.

* * * * *